United States Patent [19]

McMichael et al.

[11] Patent Number: 5,683,701

[45] Date of Patent: Nov. 4, 1997

[54] PEPTIDE FRAGMENTS OF HIV

[75] Inventors: Andrew James McMichael, Horton-cum-Studley; Douglas Fraser Nixon, Headington; Alain Robert Michael Townsend, Oxford, all of England

[73] Assignee: United Biomedical, Inc., Hauppauge, N.Y.

[21] Appl. No.: 354,884

[22] Filed: Dec. 9, 1994

Related U.S. Application Data

[63] Continuation of Ser. No. 89,603, Jul. 12, 1993, abandoned, which is a continuation of Ser. No. 807,757, Dec. 17, 1991, abandoned, which is a continuation of Ser. No. 363,780, Jun. 9, 1989, abandoned.

[30] Foreign Application Priority Data

| Jun. 10, 1988 | [GB] | United Kingdom | 8813746 |
| Jul. 5, 1988 | [GB] | United Kingdom | 8815956 |
| Nov. 11, 1988 | [GB] | United Kingdom | 8826445 |

[51] Int. Cl.$^6$ .................... A61K 38/04; A61K 39/21; A61K 39/38; C07K 1/00

[52] U.S. Cl. ............ 424/208.1; 424/204.1; 424/188.1; 424/184.1; 530/326; 530/350

[58] Field of Search .................... 530/326, 350; 424/204.1, 188.1, 208.1

[56] References Cited

U.S. PATENT DOCUMENTS

| 4,554,088 | 11/1985 | Whitehead et al. | |
| 4,629,783 | 12/1986 | Cosand. | |
| 4,772,547 | 9/1988 | Heimar et al. | 435/5 |
| 4,808,536 | 2/1989 | Chang et al. | 435/5 |
| 5,459,238 | 10/1995 | McMichael et al. | |
| 5,480,967 | 1/1996 | McMichael et al. | |

FOREIGN PATENT DOCUMENTS

| 230222 | 7/1987 | European Pat. Off. |
| 284587 | 9/1988 | European Pat. Off. |
| 290893 | 11/1988 | European Pat. Off. |
| 330359 | 8/1989 | European Pat. Off. |
| 346022 | 12/1989 | European Pat. Off. |
| 356007 | 2/1990 | European Pat. Off. |
| 412766 | 2/1991 | European Pat. Off. |
| 86/02383 | 4/1986 | WIPO. |
| 86/05591 | 9/1986 | WIPO. |
| 86/06414 | 11/1986 | WIPO. |
| 88/08538 | 3/1988 | WIPO. |
| 89/02277 | 3/1989 | WIPO. |
| 91/09869 | 7/1991 | WIPO. |

OTHER PUBLICATIONS

Sternberg, FEBS Letters, vol. 218, pp. 231–237 (1987).
Mills, J. Immunol., vol. 144, pp. 1677–1683 (1990).
Bouillot et al, Nature, vol. 339, pp. 473–475 (1989).
Harlow et al, Antibodies, A Laboratory manual, Cold Spring Harbor, pp. 77, 96, 97 (1988).
Fauci et al, Annals of Internal Med., vol. 110, pp. 373–385 (1989).
Kurth, AIDS Research & Human Retroviruses, vol. 7, pp. 425–433.
Koup et al, J. of Virology, vol. 68, pp. 4650–4655 (1994).
Gotch et al, International Immunology, vol. 2, pp. 707–712 (1990).
Choppin et al, Critical Reviews in Immunology, vol. 12, pp. 1–16 (1992).
Sanchez–Madrid, PNAS US, vol. 79, pp. 7489–7493 (1982).
Ferns et al, AIDS, vol. 3, pp. 829–834 (1989).
Mathiesen, Immunology, vol. 67, pp. 453–459 (1989).
Wahren et al, J. Acquired Immune Deficiency Syndrome, vol. 4, pp. 448–456 (1989).
Parekh et al, Int. Conf. On AIDS, Jun. 4–9, 1989, p. 651.
McMichael et al, J. Exp. Med., vol. 164, pp. 1397–1406 (1986).
Gotch et al, Nature, vol. 326, pp. 881–882 (1987).
Cellular and Molecular Immunology, A.K. Abbas et al Eds., W.B. Saunders Co., Philadelphia, PA, pp. 398–401 (1991).
Immunology, Third Ed., I.M. Roitt et al Eds., Mosby, St. Louis, pp. 2.4–2.8 (1993).
Townsend et al, Cell, vol. 44, pp. 959–968 (1986), "The Epitopes of Influenza Nucleoproteins Recognized by Cytotoxic T Lymphocytes can be Defined with Short Synthetic Peptides."
Takahashi et al, Proc. Nath. Acad. Sci. USA, vol. 85, pp. 3105–3109 (1988).
Müllbacher et al, J. Immunological Methods, vol. 68, pp. 205–215 (1984).
Parish et al, J. Immunological Methods, vol. 58, pp. 225–237 (1983).
Letter of Opposition dated Nov. 1, 1996, from Peter J. Smart to European Patent Office.
Letter dated Nov. 14, 1996, from Peter J. Smart to European Patent Office.
Communication of Notice of Opposition dated Dec. 23, 1996.
Letter of Opposition dated Dec. 22, 1994, from John Raynor to European Patent Office.
Communication of Notice of Opposition dated Jan. 17, 1995.
Observations of patent proprietor relating to Notice of Opposition dated Jun. 23, 1995.
Communication from European Patent Office dated Feb. 29, 1996.
Letter from Peter J. Smart to European patent Office dated Sep. 4, 1996.

(List continued on next page.)

*Primary Examiner*—Lynette F. Smith
*Attorney, Agent, or Firm*—Oblon, Spivak, McClelland, Maier & Neustadt, P.C.

[57] ABSTRACT

Peptides are described which have the amino acid sequence of a fragment of HIV (human immunodeficiency virus) which interacts specifically with a particular human leucocyte antigen (HLA) class I molecule, to stimulate cytotoxic T lymphocyte immunity. Such fragments can be used in a potential vaccine against AIDS (acquired immune deficiency syndrome), and for diagnostic and therapeutic purposes.

3 Claims, No Drawings

OTHER PUBLICATIONS

Haynes, 1993, "Scientific and Social Issues of Human . . . " Science 260:1279–1286.

Fox, 1994, "No Winners Against AIDS". Biotechnology 12:128.

Buhni, et al, 1994, "Comparative Analysis of HIV . . . " J. Cellular Biochemistry, Suppl. 18B Abstract J306.

Webster's Ninth New Collegiate Dictionary, 1990, pp. 871, 946, 1301.

Claverie, et al, 1988, "T–Immunogenic Peptides are . . . " E. J. Immunol. 18:1547–1553.

Nixon, et al, 1988, "HIV–1 Gag–Specific Cytotoxic . . . " Nature, vol. 336: 484–487.

Walker, et al. 1987, "HIV–Specific Cytotoxic T Lymphocytes . . . " Nature 328: 345–348.

Wahren, et al., 1987, "Characteristics of the Specific Cell–Mediated . . . " J. Virol. 61(6):2017–2023.

Greene, 1993, "AIDS and The Immune System" Sep. 1993. Scientific American, pp. 99–105.

Brown, 1993, "AIDS Vaccine Trials Viewed With Caution". Wash., Post Newspaper, Jun. 10, 1993.

PEPTIDE FRAGMENTS OF HIV

This application is a Continuation of application Ser. No. 08/089,603, filed on Jul. 12, 1993, now abandoned; which was a Continuation of Ser. No. 07/807,757, filed on Dec. 17, 1991, now abandoned; which was a Continuation of Ser. No. 07/363,780, filed on Jun. 9, 1989, now abandoned.

FIELD OF INVENTION

This invention concerns peptide fragments of HIV (human immunodeficiency virus) and the use thereof in a potential vaccine against AIDS (acquired immune deficiency syndrome), and for diagnostic and therapeutic purposes.

SUMMARY OF THE INVENTION

According to one aspect of the present invention there is provided a peptide having the amino acid sequence of a fragment of HIV which interacts specifically with a particular human leucocyte antigen (HLA) class I molecule, to stimulate cytotoxic T lymphocyte immunity.

One such peptide has the sequence $NH_2$-lysine-arginine-tryptophan-isoleucine-isoleucine-leucine-glycine-leucine-asparagine-lysine-isoleucine-valine-arginine-methionine-tyrosine-cysteine-COOH, which is derived from the gag (group associated antigen) p24 protein of HIV (i.e. one of the internal core proteins) between residues 263 and 277. The carboxy-terminal cysteine is not part of the gag sequence and is added to facilitate chemical coupling reactions. This peptide interacts specifically with HLA B27, and individuals with HLA B27 (about 7% of the Caucasian population) should respond to the peptide, resulting in production of cytotoxic T lymphocytes (CTL) specific for gag and HLA B27, and capable of lysing cells infected with HIV.

Other peptides interact specifically with other HLA molecules and behave in a similar manner on individuals with the relevant HLA.

By way of explanation, it has been shown that virus proteins such as gag are presented to T cells as degraded peptide fragments (about 15 amino acids) bound to larger HLA class I molecules on the surface of infected cells. Different peptide regions (epitopes) are recognized and interact specifically with different HLA class I molecules. CTL will only recognize target cells that share HLA Class I molecules, i.e. the T cells recognize a combination of virus antigen plus self HLA. There are probably about 120 different HLA class I molecules, and each individual human has a limited selection, and so will respond only to certain epitopes.

Epitopes recognised with different HLA can be identified and isolated in known manner or made by protein synthesis using known techniques.

Peptides in accordance with the invention can be used as the basis of a vaccine against AIDS, by stimulating production of CTL responsive to the relevant HLA and so priming the CTL response.

In a further aspect the present invention thus provides a vaccine against AIDS, comprising a peptide having the amino acid sequence of a fragment of HIV which interacts specifically with a particular human leucocyte antigen (HLA) class I molecule.

The vaccine preferably comprises a peptide which interacts with a relatively common HLA class I molecule, such as HLA A2 which is found in about 40% of the population, or HLA A1, A3, B7 or B44, each of which is found in about 10% of the population.

The vaccine may comprise more than one peptide, and preferably comprises peptides responsive to some of the more common HLA class I molecules to increase effectiveness. For example, a vaccine having peptides responsive to HLA A1, A2, A3, B7 and B44 should stimulate CTL responses in about 90% of the population: the remaining 10% could be protected by herd immunity.

The vaccine may take various different forms. For example, the vaccine may comprise a peptide or mixture of peptides for administration in solution, or absorption onto insoluble material or mixing with an adjuvant. The peptide amino acid sequence could alternatively be used to construct synthetic or fusion proteins that contain the relevant peptide epitopes, by known recombinant DNA techniques. These proteins could be used to immunize as soluble protein or absorbed onto insoluble material or mixed wih adjuvant. Alternatively the sequence information could be used to construct recombinant microorganisms using known techniques which would express the relevant sequences in their own proteins. Examples would be recombinant vaccinia viruses, recombinant polio-myelitis viruses, recombinant BCG, recombinant salmonella, recombinant adenovirus.

Another use of the sequence information would be to construct analogs of the peptides, or other chemicals which would interact with (e.g., bind to) the HLA molecules involved or the T cell receptors involved and interfere with or stimulate this form of immune response. Inhibition of this type of immunity might be important if this immune response plays a harmful role in any of the pathology caused by HIV. If so it may be important to regulate the levels of this type of T cell immunity in HIV seropositive individuals so as to achieve a balance between beneficial and harmful effects. Stimulation by such agents may be an alternative way of inducing an immune response in seronegative individuals.

Peptides in accordance with the invention can also be used for diagnostic purposes. In particular, it has been found that it is possible to use the peptide in some patients to identify T lymphocyte response in a relatively simple assay. Briefly, fresh peripheral blood mononuclear cells (or lymphocytes obtained from biopsy material) are prepared and added at ratios of 50:1, 25:1 and 10:1 to $10^4$ $^{51}$-chromium labelled B lymphoblastoid cells matched for the relevant HLA molecule. The HLA type of patient is determined in known manner by tissue typing, and B lymphoblastoid cells obtained from a donor of known HLA type (again determined in known manner by tissue typing) amd transformed with Epstein Barr using known techniques. A peptide in accordance with the invention, which interacts with the relevant HLA molecule, is also added to the cells in a concentration of 10 to 100 u molar. After 4 hours incubation the supernatant is removed and the released $^{51}$-chromium measured. The $^{51}$-chromium released is compared to that released by incubation of labelled cells in detergent, which gives a maximum value, and released by labelled cells incubated in medium alone, which gives a minimum value. If lysis (defined by $^{51}$-chromium relase of at least two times the minimum value) is observed it means that there are cytotoxic T lymphocytes in the patients' mononuclear cells and these are likely to be indicative of infection with HIV.

Such an assay, together with antibody measurements, may also be useful for measurement of the patient's general immune response to HIV, and may have prognostic implications. This approach may represent a very simple method which can be used for measuring cell mediated immunity in HIV seropositive patients. It may also be possible to automate the method.

Hence, in a further aspect the present invention provides a method of assaying cells for the presence of cytotoxic T lymphocytes, comprising incubating cells with labelled B lymphoblastoid cells matched for HLA type in the presence of a peptide in accordance with the invention which interacts with the relevant HLA type, and determining the amount of label released.

By comparing the amount of released label with known standards an indication of the degree of lysis can be obtained and hence of likely infection with HIV.

Peptides in accordance with the invention also have potential use in therapy. Such peptides (and other peptide epitopes that we have identified previously in our studies on influenza virus) have been used to stimulate cytotoxic T lymphocytes to grow in vitro. The method involves exposing cultured peripheral blood mononuclear cells, wich contain cytotoxic T lymphocytes, to autologous cells, mononuclear cells or B lymphoblastoid cell lines, which have been treated for one hour with an appropriate peptide in accordance with the invention at approximately 10–100 ug/ml then washed in tissue culture medium and irradiated to 3000 rads. The cells are then cultured in the presence of interleukin-2 at 10 units/ml. Using this method cytotoxic T lymphocyte cell lines specific for the peptide have been grown, and these lines have been expanded up to $10^8$ cells. These expanded cytotoxic T Cell lines could be used to treat patients by reinfusion.

Preliminary data indicates that patients with AIDS or the AIDS related complex show low levels of cytotoxic T cell activity, whereas those who are infected with HIV but are healthy show high levels. Part of the immune deficiency syndrome therefore may be a result of impaired cytotoxic T cell activity. The proposal therefore would be to reinfuse autologous cytotoxic T cells grown in vitro on synthetic peptide pulsed cells. Initially patients who had previously had a high cytotoxic T cell activity would be treated at a stage when their levels of these cells was declining. The cytotoxic T cell lines could be prepared from frozen lymphocytes taken earlier in the patient's infection.

Thus in another aspect the invention provides a method of treating a patient for AIDS or related conditions, comprising administering cytotoxic T cells treated with peptide in accordance with the invention which interacts with a HLA molecule present in the patient.

The cytotoxic T cells are preferably derived from lymphocytes taken from the patient at an earlier stage. The lymphocytes may be stored in frozen condition until used for preparation of the cytotoxic T cell line.

The peptide epitope from HIV gag p24, restricted by HLA-B 27 is found to be quite well conserved between different strains of HIV 1 and HIV 2, and it was found that cytotoxic T lymphocytes from a patient infected with HIV 1 cross-reacted on the HIV 2 peptide sequence. This means that this peptide and other peptide epitopes from similarly conserved parts of the virus, may be useful in vaccines to stimulate protection against both HIV 1 and HIV 2, and also for diagnostic and therapeutic purposes with patients infected with HIV 1 and/or HIV 2. It is thought that at least 50% of such epitopes will be conserved in this way.

The invention will be further described, by way of illustration, in the following example.

EXAMPLE

Work was carried out on the peptide with the sequence NH$_2$-lysine-arginine-tryptophan-isoleucine-isoleucine-leucine- glycine-leucine-asparagine-lysine-isoleucine-valine-arginine-methionine-tryosine-cysteine-COOH. The peptide is derived from the gag p24 protein of HIV between residues 263 and 277. The carboxy-terminal cysteine is not part of the HIV gag sequence and was added to facilitate chemical coupling reactions. It may be possible later to define this peptide even more precisely, determining an optimum of 10–12 amino acids.

A way has been worked out of stimulating the circulating precursors of cytotoxic T lymphocytes in peripheral blood to develop into active cytotoxic T lymphocytes, specific for HIV in vitro. This is described in more detail below, but briefly involves stimulating a small fraction of the peripheral blood lymphocytes with the mitogen. phytohaemagglutinin (PHA) for 24 hours and then adding these cells to the remaining lymphocytes. The PHA activation probably activates the HIV genome so that HIV vital proteins are synthesized. After culture for seven days, cytotoxic T lymphocyte activity can be measured by killing on autologous target cells (Epstein Barr virus transformed B lymphoblastoid cell lines) that have been infected with recombinant vaccinia viruses that express single HIV proteins.

It has been shown that 70–80 per cent of HIV seropositive donors give a cytotoxic T lymphocyte response to the gag protein, expressed by recombinant vaccinia virus. This cytotoxic T lymphocyte response is HLA restricted which means that when target cells are prepared from unrelated individuals, only those that share HLA class I antigens with the responding T cell are lysed. It has been possible to grow these cytotoxic T lymphocytes in T cell growth factor, which contains the lymphokine Interleukin-2, for up to four weeks.

Having established these HIV gag specific cytotoxic T cell lines, it was possible to test whether they could lyse autologous target cells in the presence of short (up to 20 amino acids) synthetic peptides based on the HIV gag sequence. Previous work has shown that virus proteins such as gag are presented to the T cells as degraded peptide fragments bound to the HLA class I molecules on the surface of infected cells. Following the principles previously discovered and published (Townsend et al, Cell 44:959–968, 1986, McMichael et al, J.Exp. Med. 164: 1397–1406, 1986 and Gotch et al, Nature 326:881–882, 1987) the cytotoxic T lymphocytes, the uninfected target cells and each synthetic peptide were mixed at a final concentration of 10 ug/ml. In the presence of the correct peptide the target cells are lysed and gag peptide 263-277 was recognized by cytotoxic T lymphocytes specific for gag and HLA B27. it has been shown previously for influenza virus that there are different peptide regions (epitopes) recognized according to the HLA class I molecule involved. For HIV we have defined the above peptide which is associated with the HLA antigen B27. From our previous work with influenza virus we anticipate that all or most individuals with HLA B27 who respond to HIV, will recognize this particular peptide.

This method of finding epitopes can be used to find others that will associate with different HLA class I molecules. The same principle can be applied for any other HIV protein.

Preparation of peripheral blood lymphocytes and induction of HIV specific CTL 40 ml venous blood from HIV seropositive donors was placed in heparinised containers (100 ul of 100 units/ml preservative free heparin) and was diluted 2:1 with RPMI 1640 tissue culture medium (Gibco) supplemented with 100 units/ml penicillin and 200 ug/ml streptomycin, in the absence of serum.

5 ml of lymphocyte separation medium (LSM, Flow Laboratories) was carefully underlayed under 15 ml of blood/media mixture on a sterile plastic 25 ml universal container. The tube was centrifuged at room temperature at 1200 rpm for 30 minutes after which time peripheral blood mononuclear cells (PBMC) were removed from the interface. The PBMC were washed twice with RPMI-1640 then resuspended in 8 ml RPMI 1640+10% foetal calf serum ("R10") and counted. ⅛th of the PBMC were incubated in 50 ml flasks (Falcon) with added R10 to a concentration of $1.5 \times 10^6$ cells/ml. Phytohaemagglutinin (PHA—Wellcome Diagnostics) was added at 1/200 final concentration (2 ug/ml). These cells were incubated at 37° C. in 5% $CO_2$ in air for 24 hours. The remaining ⅞th of the PBMC were cultured at a concentration of $1.5 \times 10^6$/ml in R10 at 37° C. in 5% $CO_2$/air in a 50 ml tissue culture flask.

After 24 hours the PHA stimulated cells were washed twice in R10, resuspended in R10 at $1.0 \times 10^6$/ml and added to the unstimulated cells. The cultures were left in the incubator for seven days prior to use in the cytotoxic T cell assay. After seven days T cell growth factor (Lymphocult T; Biotest) was added to the culture at 10 units/ml and the growing cells were kept at $0.5-1 \times 10^6$/ml, being fed with R-10 plus 10 u/ml T cell growth factor every 3 days.

Preparation of Target Cells

Epstein Barr virus transformed B lymphoblastoid cell lines, autologous matched or mismatched at HLA class I were washed and resuspended to $1-5 \times 10^6$/100 ul in R10. 300 uCi $Na_2{}^{51}CrO_4$ ($Cr^{51}$ Amersham) was added and the cells incubated for one hour at 37° C. in 5% $CO_2$-air. The cells were washed once and then resuspended in peptide solutions (peptide stock dissolved in R10 at 1 mg/ml) at a final concentration of 10 ug/ml. Each peptide was tested separately. Each mixture was incubated for one hour at 37° C. in 5% $CO_2$-air, then the cells were washed three times, made up to $2 \times 10^5$ cells/ml in R10 and dispensed into microtitre trays (96 well round bottom-Nunc).

As controls the autologous B lymphoblastoid cell lines were either uninfected and not peptide treated (negative control) or infected with recombinant vaccinia virus (10 pfu/cell for 4 hours at 37° C. in 5% $CO_2$ in air) (positive control) (McMichael et al, J.Gen. Virol 67:719, 1986).

Preparation of Effector Cells

Cells were harvested by centrifuging at 1500 rpm for 5 minutes and resuspended in R10 for use in the CTL assay.

CTL Assay

Target cells were dispensed at $10^4$ cells/well in 96 well round bottomed micro-titre trays in 50 ul R10 and effector cells were added in 100 ul of the same medium.

Experimental wells were dispensed in duplicate. Controls for background $^{51}Cr$ release in the absence of the effector cells (medium controls) and maximal $^{51}Cr$ release in the presence of 5% triton X-100 (detergent controls) were plated in quadruplicate. Plates were incubated for 4 hours at 37° C., 75 ul supernatant was removed into small tubes for counting on the gamma counter. 75 ul 10% chloros was added prior to removal from the containment laboratory. Lysis was calculated from the formula:

$$\% \text{ specific lysis:} \frac{\text{experimental counts} - \text{medium control}}{\text{detergent control} - \text{medium control}} \times 100$$

Spontaneous $^{51}Cr$ release by target cells in medium alone varied between 8%–30% of count released by triton X-100.

What is claimed is:

1. A pharmaceutical composition, comprising a peptide having the sequence $NH_2$-lysine-arginine-tryptophan-isoleucine-isoleucine-leucine- glycine-leucine-asparagine-lysine-isoleucine-valine-arginine-methionine-tyrosine-COOH and a pharmaceutically acceptable carrier.

2. A composition according to claim 1, wherein the peptide additionally comprises a C-terminal cysteine residue.

3. A composition according to claim 1, comprising a peptide epitope which interacts with an HLA Class I molecule selected from the group consisting of: HLA A1, A2, A3, B7 and B44.

* * * * *